United States Patent [19]

Becket

[11] Patent Number: 5,389,546

[45] Date of Patent: Feb. 14, 1995

[54] METHOD FOR DETERMINING AND MONITORING CONSTITUENT CONCENTRATION OF AN AQUEOUS METALWORKING FLUID

[75] Inventor: Giles J. P. Becket, Cincinnati, Ohio

[73] Assignee: Cincinnati Milacron Inc., Cincinnati, Ohio

[21] Appl. No.: 230,445

[22] Filed: Apr. 20, 1994

Related U.S. Application Data

[63] Continuation of Ser. No. 891,118, Jun. 1, 1992, abandoned.

[51] Int. Cl.$^6$ .......................................... G01N 31/16
[52] U.S. Cl. ...................................... 436/51; 436/43; 436/50; 436/52; 436/163; 422/75; 422/77
[58] Field of Search ............... 436/43, 50, 51, 52, 436/163; 422/75, 77

[56] References Cited

U.S. PATENT DOCUMENTS

| | | | |
|---|---|---|---|
| 2,668,097 | 2/1954 | Hallikainen et al. | 23/253 |
| 3,308,041 | 3/1967 | Strickler | 204/1 |
| 4,120,657 | 10/1978 | Nagy et al. | 23/230 R |
| 4,165,218 | 8/1979 | Vanhumbeeck et al. | 23/230 R |
| 4,695,431 | 9/1987 | Farrell | 422/81 |
| 4,798,803 | 1/1989 | Wolcott et al. | 436/52 |
| 4,816,303 | 3/1989 | Koroecke et al. | 428/333 |
| 4,900,683 | 2/1990 | Metzger et al. | 436/179 |
| 4,950,610 | 8/1990 | Tittle | 436/163 |
| 4,999,305 | 3/1991 | Wolcott et al. | 436/52 |
| 5,004,696 | 4/1991 | Clinkenbeard | 436/51 |
| 5,046,028 | 9/1991 | Bryan et al. | 364/550 |
| 5,139,956 | 8/1992 | Schick et al. | 436/52 |

FOREIGN PATENT DOCUMENTS

| | | | |
|---|---|---|---|
| 2222164 | 11/1972 | Germany | G01N 27/56 |
| 2000884 | 1/1979 | United Kingdom | G05D 21/00 |
| 2062223 | 5/1981 | United Kingdom | . |
| 2210033 | 6/1989 | United Kingdom | B01D 53/34 |
| 2215327 | 9/1989 | United Kingdom | C02F 1/52 |

OTHER PUBLICATIONS

Detection of PH of Alkaline Solution Containing Metalliccomplex Compounds W/Ethylene Diamine—Abstr. No. 59-176654, Oct. 6, 1984, Pat. Abst. of Japan vol. 9, No. 33 (Feb. 13, 1985).
Controlling and Administering Metod of Etching Solution—Abst. No. 59-1679, Jan. 7, 1989, Pat. Abst. of Japan, vol. 8, No. 77 (Apr. 10, 1984).
Potentiometric Detection System for Flow Injection Titrimetry, S. F. Simpson et al. Analytical Chemistry, vol. 54, No. 1, (Jan. 1982), pp. 43–46.
Injection Techniques in Dynamic Flow Through Analysis With Electroanalytical Sensors, Erno Pungor et al, Analytical Chmica Acta, 104 (1979) pp. 1–24.
Flow Injection Analysis—Part IX. A New Approach To Continuous Flow Titrations, J. Ruzicka et al, Analytica Chimica Acta, 92 (1977) pp. 235–249.
Flow Injection Analysis—Part I. A New Concept of Fast Continuous Flow Analysis, J. Ruzicka et al, Analytica Acta, 78 (1975) pp. 145–157.
ADI 2011 Titrolyzer—Applikon Dependible Instruments by—product bulletin.
FPA 300 Series Field Programmable Analyzer—Tytronics Inc.—product bulletin.

*Primary Examiner*—Jeffrey R. Snay
*Assistant Examiner*—Harold Y. Pyon
*Attorney, Agent, or Firm*—John W. Gregg; Donald Dunn

[57] ABSTRACT

The total alkalinity of an aqueous metalworking fluid is monitored and controlled by a continuous titration method that continuously supplies a stream of the metalworking fluid, at a known, controllable flow rate, to a flow through chamber having therein a static mixing element. Simultaneously and separately a stream of acid titrant, of known acid concentration is injected into the flow through chamber at a known controllable flow rate. The acid titrant and metalworking fluid mix and react in the chamber and the reacted metalworking fluid exiting the chamber passed over the tip of a pH electrode. The pH of the reacted metalworking fluid is continuously monitored and the output of the pH electrode used to adjust the flow of acid titrant to the chamber until an endpoint pH valve (typically a pH of 4) is reached. The total alkalinity is then determined from a) the known flow rates of the aqueous metalworking fluid and acid titrant and the known acid concentration of the titrant or may be determined from calibration curves for XY coordinate plots of volume of titrant vs known metalworking fluid concentration.

11 Claims, 1 Drawing Sheet

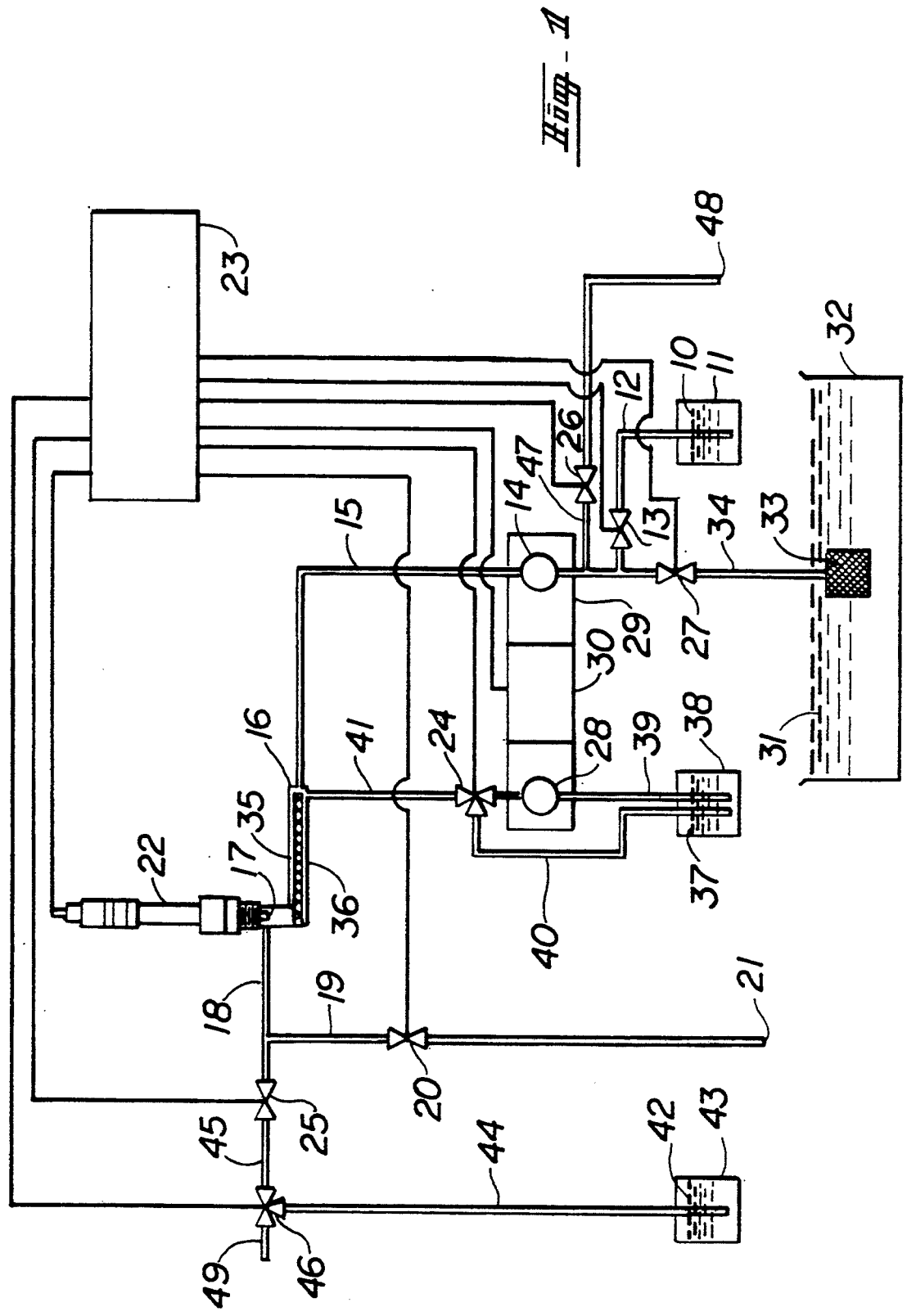
Hüp-1

METHOD FOR DETERMINING AND MONITORING CONSTITUENT CONCENTRATION OF AN AQUEOUS METALWORKING FLUID

This is a continuation of copending application(s) Ser. No. 07/891,118 filed on Jun. 1, 1992, now abandoned.

FIELD OF INVENTION

This invention relates to the art of monitoring and controlling multicomponent aqueous metal working fluids applied to the metal workpiece/tool interface in the physical shaping of metallic articles. Background In the shaping of a solid workpiece, such as for example a piece of metal, into a useful article it is known to apply a cutting or non-cutting tool against the workpiece. This tool and/or the workpiece may be rotated with respect to each other, often at high speeds. Such high speeds are typically found in turning and grinding operations for shaping metals and other solid materials. In other cases the tool and workpiece are caused to have sliding contact with each other such as in a punching operation. Still other shaping operations cause a tool to be applied against the workpiece with great force without cutting the workpiece, such as in a metal rolling and drawing and ironing processes. High heat and friction are generated during these and other shaping methods causing such problems as tool wear, distortion of the finished article, poor surface finish and out of tolerance dimensions for the article. High Scrap rates, tool wear and increased costs result from these problems. To overcome these and other problems it is known in the art to apply a metalworking fluid to the interface between the tool and the workpiece. The metalworking fluid has a number of attributes including cooling the tool and workpiece and reducing friction between the tool and workpiece. As used in this disclosure and claims the term metalworking fluid shall mean a complex aqueous liquid applied to the interface between a tool and a metallic workpiece during the shaping of the workpiece by physical means. The physical means are principally mechanical means and are exemplified by grinding, machining, turning, rolling, punching, extruding, spinning, drawing and ironing, pressing and drilling operations.

The metalworking fluids applied to the interface between the tool and the workpiece, in the metalworking art can be broadly classified into two categories. These categories are oils and aqueous based liquids or fluids. The oils are non-aqueous liquids comprising an oil or mixture of oils and one or more additives such as for example extreme pressure agents, corrosion inhibitors, bactericides, fungicides and odor control agents. Aqueous based metalworking liquids are complex combinations of water, lubricant and additives such as for example surfactants, extreme pressure agents, corrosion inhibitors, bactericides and fungicides. Many different lubricants are used in the aqueous based metalworking liquids and the aqueous metalworking fluids classified as soluble oils, synthetic and semi synthetic fluids. The lubricants and many other components of the aqueous based metalworking liquids are synthetic or naturally occurring organic compounds or mixtures of compounds. Lubricants used in the aqueous based metalworking liquids may include for example esters, amides, polyethers, amines and sulfonated oils. The lubricant component reduces friction between the tool and workpiece while the water helps dissipate the heat generated in the metalworking operation. Corrosion inhibitors are employed to reduce or prevent corrosion of the workpiece and finished article as well as to reduce or prevent chemical attack on the tool. Bactericides and fungicides are used to reduce or prevent microbial or fungal attack on the constituents of the liquid, while the surfactant may be employed to form a stable suspension of water insoluble components in the water phase of the liquid. Thus each component has a function contributing to the overall utility and effectiveness of the metalworking liquid. Typically the aqueous based liquid has a high pH (i.e. a pH greater than 7) and therefore is alkaline in nature.

During its use an aqueous based metalworking fluid may undergo numerous changes. These changes are primarily alterations of the various components of the fluid caused by heat, oxidation, contamination, biological attack and reaction with metal chips or other contaminants. Decomposition of components induced by heat, oxidation resulting from contact with air, reaction with metal chips contaminating the fluid, microbial or fungicidal induced changes, evaporation of water and plating out of constituents individually and collectively may occur during the storage and use of the fluid. Many of these changes are combated by employing materials highly stable to heat and oxidation, and by the use of stabilizing agents such as antioxidants, fungicides and bactericides. However, changes in the fluid continue to occur during storage and use to some lessor or greater degree. The most pronounced and rapid changes occur during the use of the fluid in a metalworking operation, leading to reduced beneficial performance and reduced useful life of the fluids. Decomposition and/or modification of the lubricant component by heat, oxidation or other reactions produces increased friction and increased tool wear. Destruction or modification of the corrosion inhibitor leads to increased corrosion of the workpiece, finished article and/or tool. Changes in the fungicide or bactericide result in increased fungal and microbial attack upon the lubricant and/or other components of the aqueous based metalworking fluid composition. All of these changes, as well as evaporation of water and plating out of constituents of the fluid, produce detrimental alterations in the concentration of the components of the fluid and in turn decrease the effective performance and useful life of the fluid. Such reduction in performance shows up in increased tool wear, poor surface finish, increased scrap, heat build up and higher power consumption.

To combat the negative affects of changes in the composition of the aqueous based metalworking liquid, occurring during storage and use, it is important to monitor the physical and/or chemical conditions of the fluid on a frequent, preferably continuous basis. Such monitoring not only provides indications of changes, but also points to corrective measures to be taken to restore the effectiveness of the liquid and extend its useful life. Among the chemical and physical characteristics measured in such monitoring of the liquid are pH, dissolved oxygen, temperature, conductivity, microbial activity, surfactant or emulsifier activity, oil contamination, metal chip contamination and total alkalinity. Instrumental and wet analytical techniques are applied in the art to the measurement of these and other characteristics of aqueous metalworking fluids. These techniques are used on samples taken from a reservoir of the fluid being used in a metalworking operation, particularly a central system reservoir that supplies the fluid to a number of machine tools for shaping metals. The samples are commonly taken to a laboratory or other convenient location where the analyses and measurements are performed. Often the measurements are made at locations near or adjacent to the reservoir of metalworking fluid, particularly the outlet side of a central system reservoir feeding the machine tools. Some measurements (e.g. temperature, conductivity, pH and dissolved oxygen) are made by sensors placed in the flow path of the aqueous metalworking fluid being supplied to the metalworking machine tools. In such cases the measurements may be made on a continuous or intermittent bases. The results obtained in the analysis and measurements are utilized to determine the condition of the fluid and to take necessary corrective actions to restore the fluid to its proper condition. Such corrective action can include the addition of one or more materials to the reservoir of fluid or may include just adding more undiluted (i.e. concentrated) fluid to the reservoir of diluted fluid. Where a sample of the fluid is manually obtained from the reservoir supply feeding the metalworking machine tools of a central system and taken to a remote laboratory for analysis and measurements the process is characterized by being discontinuous, time consuming and labor intensive. This technique, because of its manual, time consuming nature, gives results that may be and often are not truly indicative of the condition of the fluid at the time corrective actions are manually determined and taken. Thus, such actions may and often do not bring a central system fluid to its proper working condition or composition. In addition to the time consumed in the manual process of obtaining a sample of fluid and performing the analysis and measurements thereon at a remote location there is to be considered the time spent in calibrations and clean up. These problems associated with the manual technique of analysis and measurements on aqueous metalworking fluids have largely been overcome by automatic, inline equipment installed on central aqueous based metalworking fluid systems to perform real time analysis and measurements on a continuous or frequent basis. This rapid, low labor monitoring technique can provide a more accurate picture (i.e. real time picture) of the condition of the fluid at the time corrective measures are determined and taken.

Among the measurements made to determine the condition of an aqueous metalworking fluid is the measurement of the pH of the fluid. These fluids are often stored in a concentrated form and later diluted to a use concentration when put into service. In both the original concentrated and diluted forms the fluid has a high pH (i.e. is alkaline). This high pH is maintained for several reasons including corrosion control and prevention and the control and prevention of microbial and fungus attack on the fluid. Although the measurement of pH indicates the acidity or basicity (i.e. alkalinity) of a system it does not in itself give a true picture of the alkaline content (i.e. total alkalinity) of an aqueous based metalworking fluid. To measure this total alkalinity the art relies upon a wet analysis method. This analysis is a batch titration method wherein a known volume of the metalworking fluid is titrated to a predetermined end point with an aqueous acid solution of known acid concentration that reacts with the alkaline constituents of the fluid. In this method the acid solution is slowly added to the sample of aqueous metalworking fluid, with agitation, until a predetermined end point (e.g. pH) is reached. The end point is determined with a pH electrode or indicating dyes. From the known volume of aqueous metalworking fluid, the known concentration of the acid solution and the measured volume of acid solution used to reach the end point there can be calculated the total alkalinity of the fluid. This is a batch type process. In the common batch process a sample of the fluid is manually taken from either a supply of concentrated fluid or a central system reservoir of diluted fluid feeding several metalworking machines. The sample is then transferred to a laboratory where a measured amount of the sample is placed in a glass beaker equipped with a magnetic stirring bar and a pH electrode coupled to a pH meter. The beaker is then placed on a magnetic stirrer, the fluid agitated and the pH of the fluid is measured. Aqueous acid solution, of known acid concentration, is then added dropwise, from a burette, to the agitated fluid until a predetermined pH reading (e.g. 4.0) is obtained, whereupon the addition of acid solution is terminated. The volume of acid used is read and the total alkalinity of the fluid calculated from the known volume of the sample of fluid, the known volume of aqueous acid solution used and known acid concentration of the aqueous acid solution in accordance with the following relationship.

$$C = \frac{(VS)(CA)}{VA}$$

where
C is the total alkalinity of the fluid equivalent to the amount of the acid consumed in the titration,
VS is the volume in liters of the aqueous metal working fluid sample,
VA is the volume in liters of the aqueous acid titrating solution and
CA is the concentration of acid in the aqueous acid titration solution in moles/liter.

It is known in the art that the batch titration process for determining the alkalinity of the aqueous metalworking fluid may be automated by having a known volume of the fluid automatically fed to a titration vessel and held therein. This vessel is equipped with a stirrer (usually a magnetic stirring bar) and a pH electrode. Aqueous mineral acid solution of known acid concentration is then automatically fed to the titration vessel of stirred fluid, at a fixed known rate. The acid reacts with the alkaline constituents of the fluid and alters (i.e. reduces) the pH of the fluid. The output of the pH electrode is fed to a processing means (e.g. computer) that is programed to stop the flow of the acid solution at a predetermined pH (e.g. 4.0). At the same time the means for feeding the acid solution to the titration vessel is linked to the same processing means to provide an input defining the volume of acid solution fed to the titration vessel up to the end point (i.e. termination of titration). From the known volume of the sample of aqueous metalworking fluid, the volume of aqueous mineral acid solution used and acid concentration of the acid solution there can be calculated in accordance with the above relationship, the alkalinity (i.e. concentration of alkaline constituents) of the fluid on a manual or automated basis. In the manual calculation direct volume read outs of the sample fluid and acid solution would be used whereas in the automated calculation the volumes could be fed to a computer programed with the known acid concentration of the acid solution. The equipment for such automated batch titration method requires a) frequent calibration and b) disassembly and cleaning after each titration to provide a clean titration vessels and cleaning of the stirring means and pH electrode. Although the batch titration method may be automated in this manner it is sufficiently slow as to essentially preclude a real time analysis of the condition of the aqueous metalworking fluid. In the absence of such real time analysis difficulty occurs in accurately adjusting the condition and/or composition of the metalworking fluid to original performance and condition standards. Several analysis and adjustments are often required when analysis data is obtained by a batch type method. These several analysis and adjustments are time consuming, costly and labor intensive. Thus batch type analysis are not favorable.

SUMMARY OF INVENTION

This invention overcomes many of the disadvantages of the prior art non-titration and batch type titration methods for determining the chemical condition of an aqueous based metalworking fluid by providing real time, labor saving, accurate analysis of the chemical condition of the fluid.

It is an object of this invention to provide a method for determining the chemical condition of an aqueous based metal-working fluid.

Another object of this invention is to provide a method for real time, dynamic titration of an aqueous based metalworking fluid to determine the chemical condition of the fluid.

A still further object of this invention is to provide a method for monitoring the chemical condition of a central system aqueous based metalworking fluid that overcomes the disadvantages of prior art non-titration and batch type titration methods.

It has been discovered that the foregoing objects and others, as will be made apparent in the following description, examples and claims, can be achieved by this invention for a method of determining the chemical condition of an aqueous based metalworking fluid comprising the steps of a) continuously feeding metal particle free aqueous based metalworking fluid to a flow through chamber, having a means for mixing therein, at a known flow rate, b) feeding a titrant, reactive with a constituent of the fluid, to the chamber at a known flow rate simultaneously with the feeding of the metalworking fluid to said chamber, c) mixing and reacting the fluid and the titrant in the chamber to produce a reacted exit stream, d) flowing the exit stream past a detector means that senses the chemical condition of the liquid product caused by the reaction between the titrant and a constituent of the aqueous based metalworking fluid and produces a signal relating to said condition and e) directing the signal to a processing means therefore. This invention is particularly suited for the online determination and monitoring of the total alkalinity of a central system aqueous based metalworking fluid or liquid feeding a plurality of machine tools. The method of this invention is also applicable to the determination and monitoring of the chemical condition of an aqueous based functional liquid used in the shaping or cutting of solid non-metallic work-pieces (i.e. stone).

BRIEF DESCRIPTION OF DRAWINGS

In the appended drawing
FIG. 1 is a schematic diagram of an arrangement of an apparatus and fluid flow paths for a practice of an embodiment of the method of this invention.

DETAILED DESCRIPTION OF INVENTION

Aqueous based metalworking fluids (i.e. liquids) in accordance with the practice of this invention are complex systems usually consisting of several constituents, each of which perform one or more specific functions in the system (e.g. lubrication, emulsification, corrosion control, antimicrobial etc). The chemical condition of the aqueous based metalworking fluid is reflected by the concentrations of these constituents. For example the loss of a lubricant constituent by decomposition, reaction or extraction may be detrimental to the effectiveness of the fluid. Thus to control and maintain such effectiveness it is important to accurately determine and therefore monitor the concentration of the lubricant. The same is true for the other constituents of the metalworking liquid (e.g. corrosion inhibitors, antimicrobial agent). Where the aqueous metalworking liquid is fed to a number of shaping and/or cutting machines and operations it is usually supplied from a central reservoir for recirculation back to the machines or operations. Such a system is commonly called a central system. Such central systems have become important in automated flexible manufacturing operations for shaping metals. With use and reuse of the metalworking liquid there occurs chemical and/or physical breakdown and/or physical loss of one or more constituents of the liquid. Since in a central system the metalworking liquid is supplied to several machine tools it becomes very important that the composition of the liquid be accurately determined and monitored. Failure to achieve such monitoring may result in machine tool breakdown, scrap parts, poor surface finish,.high tool wear, corrosion of workpieces, finished parts and machine tool surfaces and costly down time for several machine tools. Methods which remove a sample of the liquid from the central reservoir and perform analyses and/or measurements at a remote location (e.g. laboratory) are commonly termed off-line methods and inherently provide data that does not describe the current condition of the metalworking fluid because of the extended time involved in the sampling, transfer of sample to a remote location and the making of the analysis or measurements. Since the off-line methods do not provide an accurate present condition picture of the metalworking liquid composition or condition the corrective measures indicated by such data and the measures taken themselves do not restore the liquid completely to the desired condition. To combat these problems online methods are employed wherein measurements are made by detectors (ego pH, temperature, refractive index, conductivity and biological oxygen demand) are placed in the flow path of the liquid being supplied to the machine tools from the central reservoir. Such sensors can provide real time data and therefore more accurately de, scribe the condition of the metalworking liquid than the same off-line measurements, for taking corrective action to more reliably maintain the liquid at the desired condition. However there are certain limitations on the accuracy and usability of online measurements that do not determine (directly) the concentrations of the constituents of the fluid (e.g. the alkaline constituents of the fluid).

This invention seeks to overcome the, time problems of off-line methods or batch methods and limitations of non-concentration indicating online methods of determining and monitoring the chemical condition of an aqueous based metalworking liquid by providing a dynamic titration method for determining and monitoring the chemical condition of an aqueous metalworking fluid comprising the steps of a) feeding metal particle free aqueous metalworking fluid to a flow through chamber, having therein a static means for mixing, at a known flow rate.

b) feeding a titrant, of known concentration and reactive with a constituent of the fluid, to the chamber at a measurable flow rate simultaneously with the feeding of the fluid to the chamber, c) mixing the fluid and the titrant in the chamber, d) reacting the fluid with the titrant in the chamber to produce a reacted exit stream, e) flowing the exit stream past a detector, in measurement proximity thereto, that senses the condition of the stream caused by the reaction between a constituent of the fluid and the titrant and generates a measurement signal related to said condition, f) directing the measurement signal to a means for processing same, g) producing a command signal for adjusting the flow rate of the titrant in response to the measurement signal, h) adjusting the flow rate of the titrant in response to the command signal until a predetermined measurement signal is obtained, and i) terminating the adjustment of the flow rate of the titrant at said predetermined measurement signal.

In a particular aspect of this invention there is provided a method for measuring the chemical condition of an aqueous based metalworking fluid composition of a central system supplying said fluid to a plurality of metalworking machine tools comprising the steps of:

a) feeding a stream of metal particle free aqueous based metalworking fluid of a central reservoir of said fluid to a flow through chamber, having therein a static means for mixing, at a known flow rate, b) feeding a titrant, of known concentration and reactive with a constituent of the metalworking fluid, to the chamber at a measurable (known) flow rate simultaneously with the feeding of the fluid to the chamber, c) mixing the fluid and the titrant in the chamber, d) reacting the fluid with the titrant in the chamber to produce a reacted exit stream, e) flowing the exit stream past a detector, in measurement proximity thereto, that senses the condition of the stream caused by the reaction between a constituent of the fluid and the titrant and generates a measurement signal related to said condition, f) directing the measurement signal to a means for processing same, g) producing a command signal for adjusting the flow rate of the titrant in response to the measurement signal, h) adjusting the flow rate of the titrant in response to the command signal until a predetermined measurement signal is obtained, and i) terminating the adjustment of the flow rate of the titrant at said predetermined measurement signal.

In a more particular practice of the invention there is provided a method for measuring the total alkalinity of an aqueous based, alkaline constituent containing metalworking fluid composition of a central system supplying said liquid to a plurality of metalworking machine tools comprising the steps of:

a) feeding the aqueous based metalworking fluid composition of a central reservoir of said fluid to a flow through chamber, having therein a static means for mixing, at a known flow rate, b) feeding an aqueous mineral acid solution of known acid concentration and reactive with an alkaline constituent of the liquid to the chamber at a measurable (known) rate simultaneously with the feeding of the liquid to said chamber, c) mixing the fluid and acid solution in the chamber, d) reacting the alkaline constituent of the fluid with the acid solution in the chamber to produce a reacted exit stream, e) flowing the exit stream in contact with a pH electrode to generate a signal related to the pH of the exit stream, f) directing the signal produced by the pH electrode to a means for processing same, g) producing a command signal, for adjusting the flow rate of the acid solution, in response to the signal from the pH electrode, h) adjusting the flow rate of the acid solution in response to the command signal until a predetermined pH electrode signal is obtained and i) terminating the adjustment of the flow rate of the acid solution at said predetermined pH electrode signal.

In a still further and preferred practice of this invention there is provided the method measuring and monitoring the chemical condition of an aqueous metalworking fluid composition comprising the steps of:

a) feeding a metal particle free aqueous metalworking fluid composition continuously to a flow through chamber, having therein a static means for mixing, at a known flow rate, b) feeding a titrant, of known concentration and reactive with a constituent of the fluid, to the chamber at a measurable (known) flow rate simultaneously with the feeding of tile fluid to the chamber, c) mixing the fluid and the titrant in the chamber, d) reacting a constituent of the fluid with the titrant in the chamber to produce a reacted exit stream, e) flowing the exit stream past a detector, in measurement proximity thereto, that senses the condition of the fluid resulting from the reaction of a constituent of the fluid with the titrant and generates a measurement signal related to said condition, f) directing the signal to a processing means therefor, g) producing a command for adjustment of the flow rate of the titrant in response to the signal, h) adjusting the flow rate of the titrant in response to the command until a predetermined measurement signal is obtained, i) generating a termination signal that stops the adjustment of the flow rate of the titrant at the predetermined measurement signal, j) passing a cleaning agent through the mixing chamber and over the exit stream contacting surfaces of the detector, k) injecting air into the cleaning agent and l) expelling cleaning agent from the detector and mixing chamber.

The steps of the method of this invention are preferably carried out in an automatic manner under the direction and control of a programmed computer. Such computer controlled automatic functioning of the method is preferably applied to the measurement and monitoring of the total alkalinity of an aqueous metalworking fluid.

In one practice of the computer controlled automatic operation of the method of this invention a suitably programmed computer, that is connected through appropriate interface circuits and control devices to an apparatus comprising 1) pumps, 2) valves, 3) an open ended, flow through tubular mixing chamber having therein a static ribbon mixing element and 4) a pH electrode positioned at the outlet side of the mixing chamber, is activated and the pH electrode of the apparatus is first calibrated by automatically passing a buffer solution over the end of the electrode. The pH of the buffer solution is measured and the measured value compared to the known pH of the solution for calibrating the pH electrode. Buffer solution may then be expelled from the apparatus by passing the aqueous metalworking fluid through the flow path of the buffer solution. The buffer solution and metalworking fluid flush are passed to a waste container. The pump and valves connecting a reservoir of aqueous metalworking fluid to the mixing chamber are then automatically activated and aqueous metalworking fluid continuously fed at a constant, measured flow rate to the flow through mixing chamber and over the pH electrode. Simultaneously the pump and valves connecting a supply of aqueous hydrochloric acid of known concentration (typically 0.2M) to the flow through mixing chamber are automatically activated and the aqueous hydrochloric acid fed at a controllable measured flow rate to the mixing chamber. A reaction between an alkaline constituent of the aqueous metalworking fluid and the hydrochloric acid in the mixing chamber produces a reacted metalworking fluid exit stream from the mixer that contacts the end of the pH electrode placed in the flow path of the exit stream and hence passes into a waste container. An electrical signal produced by the pH electrode, coming in contact with the exit stream from the mixing chamber, is fed to an interface circuit, linked to the computer, for inputting the signal strength into the computer program. Optionally the electrical signal from the pH electrode may be fed to a pH meter where it is converted to pH units readings on the meter. The computer program compares the signal strength from the pH electrode to the signal strength required for the predetermined pH end point value (typically 4) and issues a command signal to a control device that adjusts the flow rate of the hydrochloric acid solution being fed to the mixing chamber. Adjustments of the flow rate of the hydrochloric acid solution are repeated until the strength of the electrical signal produced by the pH electrode reaches a value corresponding to the predetermined end point pH. At this point the flow rates of the aqueous metalworking fluid and the aqueous hydrochloric acid solution are measured and the values fed into the computer program and combined with the previously inputted concentration of the hydrochloric acid for calculating the total alkalinity of the metalworking fluid. Simultaneously the flows of metalworking fluid and hydrochloric acid are terminated and appropriate valves closed. A pump and valves connecting a supply of cleaning agent to the mixing chamber, pH electrode and the flow path for the reacted product exit stream are now automatically activated to feed the cleaning agent to and clean the interior of the mixing chamber, the end of the pH electrode and the flow path of reacted product exit stream. To improve the cleaning action of the cleaning agent bursts of air are fed into the flow path of the cleaning agent at or near its start. A rinse solution is then passed through the mixing chamber, over the pH electrode and through the flow path of the reacted metalworking fluid exit stream. At this point the method is ready to be repeated. It may be only necessary to carry out the pH electrode calibration on some regular basis rather than every time the method is repeated. This scheduled calibration can be included in the computer programs. The measured total alkalinity value may be a) electronically stored, b) printed out or c) compared to a standard value for making manual or automatic adjustments in the composition of the aqueous metalworking fluid. This method is particularly advantageous for the online, real time measurement and monitoring of the total alkalinity of a central system supplying aqueous metalworking fluid from a central reservoir of the fluid to a number of machine tools for shaping metallic workpieces. Although the automatic pH electrode calibration step and automatic cleaning step described above are highly desirable they are not required steps in the method of this invention.

Various apparatus and fluid flow configurations may be employed in the practice of the steps of the method of this invention. In accordance with one such configuration this invention was practiced as follows, with reference to FIG. 1.

Starting with clean pump (14), conduit (15), mixer (16) and pH electrode tip (17), valves (20) and (13) were opened and valves (27) (24) (25) and (26) were closed on command signals from programmed controller (23) to begin a pH electrode calibration. Aqueous potassium acid phthalate buffer solution (10), typically having a known pH of 4, was withdrawn from reservoir (11) through conduit (12) and valve (13) by peristaltic pumps (14) and passed through conduit (15), through mixer (16), over pH electrode tip (17), through conduits (18) and (19) and through valve (20) to waste (21). The pH of the buffer solution (10) was continuously measured by pH electrode (22) and its output fed to programmed controller (23). A steady state pH reading over a 30 second interval was then compared to the known pH value of the buffer solution previously programmed into programmed controller (23). Adjustments were then made by the programmed controller in the titration pH measurements for the differential between the measured and known pH values for the buffer solution. Pump (14) was stopped and valve (13) was closed. Valves (24), (25), and (26) were placed in the closed or off position and valves (27) and (20) were placed in the on or open position by programmed controller (23). Valves (13), (20), (25), (26) and (27) were two way solenoid valves having an open and closed position. The normal position being the closed position. Valves (24) and (46) were 3 way solenoid valves having an inlet port and two outlet ports. In the normal position one of the outlet ports was closed while the inlet and the other outlet ports remained open. Valves (24) and (46) were operated by pulses of electricity at a frequency of 5 Hertz upon command from programmed controller (23). Valve (24) was selected to operate in a duty cycle range of from 10% to 90%. Duty cycle is defined as the time the valve remains open during an open to close to open cycle divided by the total time of a single cycle. A single cycle is the total time duration from the beginning of the opening of the valve to the next opening of the valve. Operating at a pulse frequency of 5 Hertz the cycle time of the valve (24) is 200 milliseconds. Thus the percent duty cycle of valve (24) would be the duration of the open position divided by 200 and multiplied by 100%. Peristaltic pumps (14) and (28) of pump assembly (29) were activated by drive (30) on a command signal from programmed controller (23). Cimstar 40, a semi-synthetic aqueous, metalworking fluid (31) was then continuously pumped by peristaltic pump (14) from reservoir (32) through filter (33), conduits (34) and (15)

and valve (27) to the entrance end of flow through mixer (16), having open ended 75 mm tubular housing (35) and a double helix static ribbon mixing element (36), at a programmed constant known flow rate. Cimstar is a registered trademark of Cincinnati Milacron Inc. Cimstar 40 metalworking fluid (31) was passed through mixer (16), over pH electrode tip (17), through conduits (18) and (19) and valve (20) to waste (21). The pH of the metalworking fluid (31) was measured by pH electrode (22) and the electrical signal produced by pH electrode (22) fed to programmed controller (23). During this time interval peristaltic pump (28) has been pumping 0.2 molar (0.2M) aqueous hydrochloric acid titrant solution (37) from reservoir (38) through conduit (39), three way valve (24) and conduit (40) back to reservoir (38), three way valve (24) having been in the off or normal position for return of the titrant solution (37) back to reservoir (38). Valve (24) was a 3 port solenoid valve having a normal or off position to recirculate titrant solution (37) back to reservoir (38) and an on position to pulse feed titrant solution (37) through conduit (41) to the entrance end of mixer (16). The construction of valve (24) provided for a solenoid activated plunger to open and close ports in the valve. By feeding electrical pulses of controlled variable duration to the solenoid the plunger would open and close the ports of the valve for a duration corresponding to the duration of the electrical pulses fed to the solenoid. Thus in one position the plunger allowed flow of titrant (37) from reservoir (38) to mixer (16) while in another (i.e. normal) position the flow of titrant (37) to mixer (16) was cut off and titrant (37) directed back to reservoir (38). This operation of valve (24) produced a pulsed flow of titrant (37) to mixer (16), the duration of the pulses of titrant (37) being determined by the duration of electrical pulses fed to valve (24). Since pump (28) was operating at a constant output the flow rate of titrant (37) to mixer (16) was controlled by the duration of the electrical pulses to valve (24) in combination with the output rate of pump (28). The output rate of pump (28) and the duration of the pulses of titrant (37) were measured and processed in programmed controller (23) to establish a flow rate of titrant (37) to mixer (16) that was employed by controller (23) in determining a total alkalinity of metalworking fluid (31). Upon reaching a steady state electrical signal from pH electrode (22). i.e. a constant electrical signal for 30 seconds, during the flow of the Cimstar 40 metalworking fluid (31) programmed controller (23) caused valve (24) to switch the flow of the aqueous hydrochloric acid titrant solution (37) from reservoir (38) through conduit (39), valve (24) and conduit (41) to the entrance end of mixer (16). The Cimstar 40 metalworking fluid (31) and aqueous hydrochloric acid titrant solution (37) fed to mixer (16) were mixed by static ribbon mixing element (36) in tubular housing (35) and reacted to produce a reacted metalworking fluid that exited the mixer(16) at the end of tubular housing (35) opposite to the entrance end and adjacent to the pH electrode. This reacted metalworking fluid was caused to flow over tip (17) of pH electrode (22), through conduits (18) and (19), and through valve (20) to waste (21). The reacted metalworking fluid contacting tip (17) of pH electrode (22) caused pH electrode (22) to produce an electrical signal proportional to the pH of the reacted metalworking fluid. That electrical signal was fed to controller (23) where it was processed to produce a command signal regulating the duty cycle of the electrical pulses fed to valve (24) and hence the duration of titrant (37) pulses fed to mixer (16). Increasing the duty cycle of the pulses of titrant (37) increased the amount of titrant (37) fed to mixer (16) and hence increases the amount of the acid titrant (37) mixed and reacted with the metalworking fluid (31) and alkaline components therein. Conversely decreasing the duty cycle of the pulses of acid titrant (37) decreases the amount of acid titrant (37) mixed and reacted with metalworking fluid (31) and alkaline components therein. When the flow rates of metalworking fluid (31) and acid titrant (37) fed to mixer (16) produced a reacted metalworking fluid causing pH electrode to produce an electrical signal corresponding to an end point pH value of 4 the controller (23) terminated the adjustment of the pulse for the acid titrant (37). At this point controller (23) engaged in a number of simultaneous and/or consecutive steps or operations. It a) determined and stored or processed the duty cycle for valve (24) for computing the amount of hydrochloric acid titrant (37), b) shut down pumps (14) and (28) and c) closed valves (27), (20) and (24). Controller (23) then opened valves (25) and (26) and activated pump (14) in a reverse direction from pumping metalworking fluid (31). Pump (14) operating in the reverse direction pumped cleaning solution (42), an aqueous composition containing non-ionic emulsifier, ionic emulsifier, alkanolamine, chelating agent, ferrous corrosion inhibitor, caustic and bactericide, from tank (43) through conduits (18), (45) and (44) and valves (25) and (46), over tip (17) of pH electrode (22), through mixer (16), conduits (15) and (47) and valve (26) to waste (48) to clean the system of metalworking fluid (31), acid titrant (37) and any precipitate or oily deposits formed during the titration. Cleaner was pumped for several minutes to insure thorough cleaning of the tip (17), mixer (16) and conduits (15) and (18). To achieve more efficient cleaning, pulses of air were injected via conduit (49) into cleaning fluid (42) in conduit (45) by valve (46) operating in a manner similar to valve (24) on command from controller (23). This cleaning cycle was followed by the pH electrode calibration sequence described at the beginning of this embodiment.

In the above apparatus the programmable controller (23) was programmed to automatically provide a pH electrode calibration step at the beginning of the titration method and a cleaning step at the end of the titration method. Although these two automatic steps are highly desirable in the practice of this invention and are preferred they are not required steps in the method of this invention. Such steps may also be practiced manually.

In the above described apparatus the components and operating conditions were selected to provide the efficient, effective mixing of metalworking fluid and titrant for stable pH readings of the fluid exiting mixer (16). It is important that the components of and operating conditions for the apparatus employed for the practice of this invention be selected to provide pH reading essentially free of drift. Thus many variations in apparatus design and operation may be employed in the practice of this invention without departing from the spirit and scope of the invention.

The total alkalinity of the aqueous metalworking fluid is the total concentration of all acid titratable constituents of the metalworking fluid. One manner of expressing total alkalinity of the metalworking fluid is as the equivalent molarity of a single alkaline constituent in aqueous solution (e.g. molarity of potassium hydroxide in an aqueous potassium hydroxide solution). The total alkalinity of an aqueous metalworking fluid may also be expressed as an equivalent concentration value for the fluid. In this mode of expression the volume of titrant required to reach the predetermined pH end point during the titration of a sample of aqueous metalworking fluid of unknown concentration in accordance with the method of this invention, is compared to an X, Y coordinate plot of titrant volume vs metalworking fluid concentration for the same metalworking fluid as the sample. To obtain the X,Y coordinate plot of titrant volume vs metalworking fluid concentration for each different metalworking fluid the fresh, unused, concentrated metalworking fluid, whose concentration equivalent of total alkalinity is known, is diluted with water, distilled water may be used, to form a series of standard diluted samples having known concentration equivalent to total alkalinity. For example the fresh, unused, concentrated metalworking fluid may be diluted to 2%, 4%, 6%, 8% and 10% of the original concentration of the fresh, unused, concentrated fluid to form a series of standard samples. Each of these standard samples is then titrated in accordance with the method of this invention to a predetermined pH endpoint (e.g. pH 4). The volume of titrant required to titrate each sample is then plotted against the concentration of each sample to form an X, Y coordinate best straight line graph. The resulting best straight line graph is characteristic for each different metalworking fluid. To obtain the concentration equivalent of total alkalinity for an aqueous metalworking fluid of unknown concentration or total alkalinity the volume of titrant required for titrating the fluid of unknown concentration in accordance with the method of this invention can be a) compared to the X, Y coordinate plot for the same metalworking fluid by determining the concentration value corresponding to the titrant volume intercept with the best straight line plot of the graph or b) used in combination with the value of the slope of the straight line plot and the Y-axis intercept of the straight line plot to determine the concentration equivalent of the total alkalinity.

Both of the above methods of expressing total alkalinity can be programmed into a programmable controller or computer of an apparatus for the practice of the method of this invention. The concentration equivalent of total alkalinity is the preferred method of expressing the total alkalinity of an aqueous metalworking fluid of unknown total alkalinity because it provides a more accessible method of monitoring, controlling and adjusting the composition of an aqueous metalworking fluid, especially during the use of the fluids in metalworking operations.

When in accordance with the method of this invention the total alkalinity of an aqueous metalworking fluid is to be expressed as the equivalent molarity of a single alkaline constituent of an aqueous solution of that constituent (e.g. potassium hydroxide in an aqueous potassium hydroxide solution) the total alkalinity may be calculated in accordance with the following formula.

$$TA = \frac{(F_t)(C_t)}{F_m}$$

where
TA = total alkalinity in moles per liter,
$F_t$ = flow-rate of the acid titrant in cubic centimeters per minute,
$F_m$ = flow rate of the metalworking fluid in cubic centimeters per minute and
$C_t$ = concentration of the acid titrant in moles per liter.
This method of expressing total alkalinity of an aqueous metalworking fluid may be programmed into a programmable controller or a computer of an apparatus for the practice of the method of this invention.

The concentration equivalent of total alkalinity method described above for expressing total alkalinity was employed with the above described apparatus of FIG. 1 and the method of this invention used therewith for the total alkalinity determination of various aqueous metalworking fluids by first establishing a calibration curve for each metalworking fluid. This calibration curve was obtained by diluting fresh, unused, concentrated metalworking fluid to form samples at various concentrations (e.g. 0.5, 1.0, 2.0, 4.0, 5.0, 6.0, 8.0, 10.0, 12.0 and 14.0 percent by volume). Each of these samples was then titrated using the apparatus of FIG. 1 in the practice of the method of this invention. The duty cycle of valve (24) of FIG. 1 corresponding to the amount of titrant for reaching the preestablished pH endpoint for each sample was plotted against the concentration value of the sample in an X, Y coordinate plot. The best straight line was drawn connecting the points of the plot to define a calibration curve for the metalworking fluid. Calibration curves were prepared for Cimstar 40, Cimstar 3700T, Cimperial 1010, Cimtech 100, Cimflo 33HP and Cimsar Qualstar aqueous metalworking fluids using the apparatus of FIG. 1 in the practice of the method of this invention. Cimstar, Cimperial, Cimtech, Cimflo and Qualstar are registered trademarks of Cincinnati Milacron Inc.

It is to be recognized that the apparatus employed in the practice of the method of this invention can place practical limitations on the scope and accuracy of the total alkalinity determination and that adjustments in conditions relating to the operation of the apparatus and the titrant (e.g. titrant concentration) may be required in respect to some aqueous metalworking fluid compositions and/or concentrations for overcoming such limitations. Thus for example in the use of the apparatus of FIG. 1 in the practice of the method of this invention the concentration of the acid titrant may require adjustment (e.g. reduction in acid concentration) in relation to the level or suspected level of total alkalinity of the metalworking fluid such that the duty cycle of valve (24) of the apparatus of FIG. 1 occurs within the range of from 10% to 90% for achieving acceptable accuracy in the total alkalinity determination. For example, very low concentrations of an aqueous metalworking fluid can have correspondingly very low total alkalinity such that the acid concentration of the acid titrant would need to be reduced to a level where the duty cycle of valve (24) of the apparatus of FIG. 1 is in the range of 10% to 90% for achieving acceptable accuracy for the total alkalinity determination. Similar adjustment in the acid concentration of the acid titrant, in the case of the practice of the method of this invention using the apparatus of FIG. 1, may be needed for determining the total alkalinity of aqueous metalworking fluids having a low or very low total alkalinity in the fresh, unused, concentrated condition.

Aqueous based metalworking fluids are complex compositions comprising a number of components that individually or in combination perform particular functions and/or impart certain characteristics to the fluid. Typically an aqueous based metalworking fluid will contain, in addition to water, one or more organic lubricant compounds, one or more emulsifiers, corrosion inhibitors, and antimicrobial and/or antifungal agents. An extreme pressure agent, an antifoaming agent, a chelating agent and an agent to facilitate the precipitation of metal particles may also be included individually and collectively in the fluid. Thus the aqueous based metalworking fluid contains a variety of organic compounds and may contain inorganic compounds. The fluid may contain water soluble and/or water insoluble constituents, the latter being present in an emulsified form. Aqueous based metalworking fluids are therefore unique systems and present their own problems and special challenges to automated, particularly real time, concentration analysis. The analysis for the concentration of one component of the fluid is often interfered with by the presence of one or more other components of the fluid.

Optical methods, for example one using a nephelometer, may be used to measure the concentration of a suspended insoluble component of a liquid composition. Such methods are also called turbidity methods and depend upon the loss of light transmitted through a standard cell containing to sample liquid as compared to the loss light through the standard cell containing a standard liquid having a known concentration of the suspended insoluble material. Aqueous metalworking fluids however often contain more than one emulsified component (i.e. suspended insoluble material) and may contain suspended contamination (e.g. oil and metal particles). Thus the determination of the concentration of one emulsified component of the metalworking fluid by an optical method, such as one using a nephelometer, is interfered with by the presence of other emulsified material in the fluid. Such an optical method would measure the total concentration of suspended matter in the fluid. The degree of color change of a dye added to a liquid system is another analytical technique employed in the measurement of the concentration of a substance in a liquid system. The intensity of the color change of the dye is proportional to the concentration of the substance being analyzed. The measured color change is compared to a table of standards to determine the concentration of the substance. This method is effective with simple liquid systems. However, in aqueous metalworking fluids one or more components can and do tie up such a dye thus removing it from the determination of the concentration of the intended constituent. Further the color and/or clarity of a metalworking fluid can interfere with the measurement of the intensity of the color change of the dye. In simple liquid systems containing non-interfering components these problems do not exist or there is a negligible effect on a concentration analysis by other components of the liquid system. This is not always true for aqueous based metalworking fluids.

Various types of complex liquid systems, such as for example nuclear waste liquids, industrial liquid waste, plating solutions and etching solutions have differing degrees of complexity, composition and physical characteristics defining unique analytical problems to be overcome for each system. Thus such complex liquid systems are analytically unique to each other such that individualistic or particular techniques and conditions are to be applied to the analysis of each such liquid system.

Many of the difficulties associated with the analysis of complex aqueous metalworking fluids, particularly those found in metalworking operations, that are associated with interference by non-analyzed components are absent in the method of this invention for determining the total alkalinity of the metalworking fluid. The method of this invention thereby provides an improvement in the monitoring, controlling and adjusting of aqueous metalworking fluids such that the useful life, effectiveness and efficiency of the fluids being used in metalworking operations is maintained or improved.

What is claimed is:

1. A method for determining and monitoring constituent concentration of an aqueous based metalworking fluid comprising the steps of
   a. supplying metal particle free aqueous based metalworking fluid, at a controllable, measurable flow rate, to a flow through chamber having a static means for mixing,
   b. supplying a titrant, reactive with said constituent of the metalworking fluid, to said chamber at a controllable, measurable flow rate and known concentration, simultaneously with and separate from the metalworking fluid,
   c. mixing the metalworking fluid and titrant in the chamber,
   d. reacting said constituent of the metalworking fluid with the titrant in said chamber to produce a reacted metalworking fluid,
   e. flowing the reacted metalworking fluid past a detector to produce an electrical signal whose strength varies in relation to the concentration of the constituent,
   f. passing said signal to a measuring means therefor that generates an electrical output related to the strength of said signal,
   g. directing said output to a means for controlling the flow rate of the titrant in relation to said signal,
   h. adjusting the flow rate of the titrant responsive to said signal until said signal reaches a predetermined value,
   i. measuring the flow rate of the metalworking fluid,
   j. measuring the flow rate of the titrant,
   k. calculating the constituent concentration of the metalworking fluid from values of the flow rates of titrant and metalworking fluid measured when the signal reaches the predetermined value.

2. The method according to claim 1 wherein the step of flowing the reacted product past a detector is a step of flowing the reacted product in contact with a pH electrode.

3. The method according to claim 1 comprising the further steps of directing the measurement of the flow rate of the metalworking fluid, the measurement of the flow rate of the titrant and known concentration of the titrant to a programmed computer.

4. The method of claim 1 comprising the step of supplying the metalworking fluid at a controllable, measurable flow rate to the flow through chamber, having therein the means of mixing, from a reservoir of metalworking fluid feeding a plurality of metalworking machines.

5. The method according to claim 1 wherein the titrant is an aqueous acid solution.

6. The method according to claim 1 further including the step of back flushing with a cleaning solution.

7. The method according to claim 2 further including the steps of passing a buffer solution through the chamber, contacting the pH electrode with the solution and flushing the pH electrode and the chamber with a rinsing agent.

8. The method of claim 2 further comprising the automatic steps of terminating the flow of metalworking fluid, terminating the flow of titrant, back flushing a cleaning solution past the detector and through the chamber to a waste fluid receiver, passing a buffer solution through the chamber and flowing the buffer solution in contact with the pH electrode.

9. The method of claim 1 wherein the metalworking fluid is an aqueous based semi-synthetic metalworking fluid.

10. The method of claim 1 wherein the metalworking fluid is an aqueous based synthetic metalworking fluid.

11. The method of claim 1 wherein the static means of mixing is a helical ribbon mixer.

* * * * *